United States Patent [19]

Williams

[11] Plant 5,115

[45] Oct. 4, 1983

[54] MINIATURE ROSE PLANT

[76] Inventor: Ernest D. Williams, 1510 Lebanon Ave., Dallas, Tex. 75208

[21] Appl. No.: 376,289

[22] Filed: May 10, 1982

[51] Int. Cl.[3] ..... A01H 5/00

[52] U.S. Cl. ..... Plt./10

[58] Field of Search ..... Plt./10

*Primary Examiner*—James R. Feyrer

[57] ABSTRACT

The subject of the present disclosure is a new and distinct variety of miniature rose plant characterized by the deep red color of the buds and flowers.

1 Drawing Figure

The present invention relates to a new and distinct variety of hardy, dwarf, bush type rose plant of the miniature class; the variety being primarily characterized—as to novelty—by deep red buds and flowers which in general color effect are similar to Big John, a miniature variety (U.S. Plant Pat. No. 4,754).

The variety is further characterized by:

An abundance of bloom, with flowers usually borne one to the stem.

Little or no fragrance.

A plant which is vigorous, of rounded somewhat upright shape with semi-glossy to matt, small foliage with pointed leaflets; the buds and flowers being similar in form and size to Beauty Secret (miniature—not patented).

The plant, which has a normal height of 14–16 inches or more, can easily be maintained at lesser height by occasional trimming.

A plant which grows and blooms satisfactorily in greenhouse, but being especially suited for outdoor culture; and provides excellent garden decoration as well as cut flowers.

The present variety of miniature rose was originated by me at my nursery located at Dallas, Tex., under conditions of careful control and observation, as a cross between Starburst (U.S. Plant Pat. No. 2,974), as the seed parent and Over the Rainbow (miniature—U.S. Plant Pat. No. 3,472) as the pollen parent.

Subsequent to origination of the variety I successfully reproduced it, at my nursery located as aforesaid, by cuttings; the reproductions having run true in all respects.

The color photograph illustrates the variety, including the foliage, buds and flowers.

Referring now specifically to the new and distinct variety of miniature rose plant, the following is a detailed description thereof in outline; all major color plate identifications being by reference to The British Colour Council Horticultural Colour Chart, except where common terms of color definition are employed.

Type: Hardy; dwarf; bushy; upright; seedling; greenhouse; outdoors; cut flowers; garden decoration; potted plant.

Class: Miniature.

*Variety name.*—Red Beauty.

Flowers borne: Usually singly on slender wirey stems.

Quantity of bloom: Abundant both outside and in greenhouse.

Bud:

*Peduncle.*—Medium to short length; slender but sturdy; erect; medium green, sometimes tinted bronze (outdoors); hairs — few.

*Before calyx breaks.*—Size — small. Form long; pointed with few to several foliaceous appendages and few tiny hairs on surface of bud; with foliaceous parts extending beyond the tip of the bud equal to one-half or more of its length. Color — medium green, occasionally tinted with bronze (outdoors).

*As calyx breaks.*—Color — deep red — becoming cream to white at base. Opening: opens well in all weather.

Bloom:

*Size when fully open.*—Small, averaging about $1\frac{1}{4}$–$1\frac{1}{2}$ inches. Petalage — double — averaging about 20 or more petals. arranged regularly plus sometimes several small petaloids. Form — high centered at first, becoming more open in the center, with petals reflexing loosely outward, with petals folded along edges to give a quilled or pointed effect. Open flowers show stamens.

Petals: Quite Thick; velvety on inside and satiny on outside surface.

*Shape.*—Outside petals, broad lanceolate with rounded tip; intermediate — broad lanceolate with rounded tip; inside — lanceolate with rounded tip.

Color: Newly opened flower from a plant grown outdoors Spring, 1982, Dallas, Tex.:

*Outside petals.*—Outside surface — near Indian Lake 826 with basal $\frac{1}{2}$ of petal white to near white (red portion often veined with near white). Inside surface — near Chrysanthemum Crimson 824/1 with large white to yellowish area at base.

*Intermediate petal.*—Outside surface — similar to outside petal. Inside surface — similar to outside petal.

*Inner petal.*—Outside surface — same as intermediate petal; inside surface — same as intermediate petal.

NOTE: The deep red, coloring of inside surface appears brighter than Chrysanthemum Crimson as there is a lighter or underneath color or veining of softer red color — similar to Cardinal Red 822 or lighter.

General color effect; newly opened flower rich velvety, deep red. Three days open — color similar to newly opened flowers but less brilliant. Behavior — opens well in all weather. Color lasts well with little fade. Spent petals drop off.

Flower longevity (Spring 1982) — plant in pot 6–8 days or longer. Cut flowers at living room temperature 4–7 days or longer.

Reproductive organs:

*Stamens.*—Abundant, arranged regularly about pistils.

*Filaments.*—Varying length, fairly short, yellow.

*Anthers.*—Well formed; yellow.

*Pollen.*—Moderate amount.

*Pistils.*—Average number.

*Styles.*—Fairly even; medium to short length; bunched.

*Ovaries.*—All enclosed in calyx.

*Hips.*—Some.

*Sepals.*—Permanent; spear shaped; recurved against peduncle.

*Seed.*—Some.

Foliage:

*Leaves.*—Compound of five (sometimes three or seven) leaflets; fairly small; leathery; semi-glossy to matt.

*Leaflets.*—Shape; broad, nearly oval; apex acute; base rounded or rounded acute. Margin serrage. Color: Medium to dark green; new growth — normal; (medium) green. Rachis: medium strength; upper side may have a few tiny short prickles or hairs, grooved; underside sparsely thorny with few or no tiny prickles. Stipules: medium long; narrow to medium width; medium length; narrow points which turn out usually at about 45 degrees or less.

Growth:

*Habit.*—Dwarf; bushy; upright; much branched.

*Growth.*—Free vigorous; internodes short.

*Canes.*—Medium; slender; sturdy.

*Main stems.*—Color: medium green.

*Thorns.*—Average; slender, nearly straight or hooked slightly downward; color — brown. Prickles — none. Hairs — none.

*Branches.*—Color; medium green, Thorns: moderate number; medium length; slender; nearly straight, inclined downward; medium oval base. Prickles: none. Hairs: none.

The miniature rose plant and its flowers as herein described may vary in slight detail due to climatic, soil and cultural conditions under which the variety may be grown; the present description being of the variety as grown at Dallas, Tex.

The following is claimed:

1. A new and distinct variety of miniature rose plant of hardy, dwarf, bushy, upright, much branched habit, substantially as illustrated and described, characterized by buds and flowers of a rich dark red color, being of a shade generally near Chrysanthemum Crimson 824/1, the buds and flowers resembling the variety Beauty Secret (not patented) in form and size but being darker red in color; and further characterized by a plant of vigorous and compact growth habit, easy to propagate from cuttings, with an abundance of small to medium size semi-glossy to matt foliage and an abundance of flowers borne usually singly on rather stiff wirey stems.

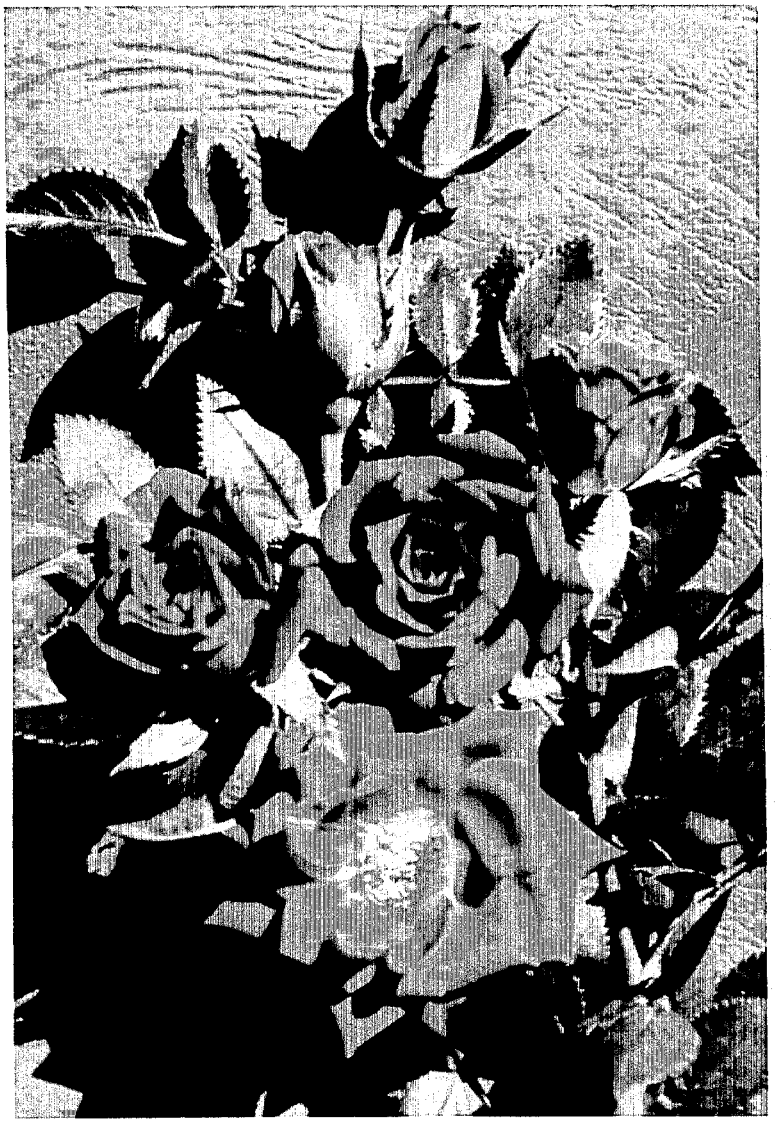

* * * * *